United States Patent [19]

Kollar

[11] 3,947,501

[45] Mar. 30, 1976

[54] PROCESS FOR TREATMENT OF REACTION MIXTURES BY HYDROGENATION

[75] Inventor: John Kollar, Wallington, N.J.

[73] Assignee: Halcon International, Inc., New York, N.Y.

[22] Filed: Apr. 5, 1974

[21] Appl. No.: 458,278

Related U.S. Application Data

[60] Division of Ser. No. 871,522, Nov. 7, 1969, Pat. No. 3,860,662, which is a continuation of Ser. No. 684,563, Nov. 20, 1967, abandoned, which is a continuation of Ser. No. 409,941, Nov. 9, 1964, abandoned, which is a continuation-in-part of Ser. No. 375,313, June 15, 1964, abandoned.

[52] U.S. Cl.... 260/618 H; 260/348.5 L; 260/617 H; 260/618 A; 260/618 C; 260/632 C; 260/632 R
[51] Int. Cl.² .................. C07C 29/00; C07C 27/10
[58] Field of Search........ 260/618 C, 618 H, 618 A, 260/348.5 L

[56] References Cited

UNITED STATES PATENTS

| 815,193 | 3/1906 | Mettler | 260/618 H |
| 3,351,635 | 11/1967 | Kollar | 260/348.5 L |

FOREIGN PATENTS OR APPLICATIONS

| 778,974 | 7/1957 | United Kingdom | 260/618 C |

OTHER PUBLICATIONS

Hawkins, "Chem. Soc."[1950], pp. 2169–2173.

*Primary Examiner*—Richard J. Gallagher
*Assistant Examiner*—D. B. Springer
*Attorney, Agent, or Firm*—William C. Long; David Dick; Riggs T. Stewart

[57] ABSTRACT

The acidic catalyst characteristics of a reaction mixture resulting from a catalytic epoxidation are reduced whereby dehydration of by-product alcohol is suppressed during subsequent work-up procedures. This reduction is effected by catalytic hydrogenation, chemical reduction or the addition of a basic material.

5 Claims, No Drawings

PROCESS FOR TREATMENT OF REACTION MIXTURES BY HYDROGENATION

This is a division of application Ser. No. 871,522 filed Nov. 7, 1969, now U.S. Pat. No. 3,860,662, issued Jan 14, 1974, which is a continuation of application Ser. No. 684,563, filed Nov. 20, 1967, abandoned, which is a continuation of Ser. No. 409,941, filed Nov. 9, 1964, abandoned, which is a continuation-in-part of Ser. No. 375,313, filed June 15, 1964, abandoned.

The present invention is concerned with the treatment of reaction mixtures which result from the metal catalyzed epoxidation of olefinically unsaturated compounds to the corresponding oxirane compound using organic hydroperoxides.

Important advances have been made in the production of oxirane compounds through the reaction of olefinic materials with organic hydroperoxides. In these processes, certain difficulties are encountered in the successful separation of products and by-products from the reaction mixtures. Specifically, the organic alcohol by-product which is formed by reduction of the organic hydroperoxide tends to undergo considerable dehydration during the subsequent recovery procedures. The alcohol dehydrates to the corresponding olefin which latter product undergoes very rapid polymerization to high-boiling residues. These residues eventually have to be removed as a useless product of the reaction. In addition, water, of course, is formed which complicates recovery procedures.

It is an object of the present invention to provide a method for the treatment of reaction mixtures resulting from the epoxidation of olefins with an organic hydroperoxide.

It is a particular object to provide a method whereby dehydration of by-product alcohol is suppressed during the effluent work-up procedures.

Other objects will be apparent from the following description of the invention.

It has been discovered that the epoxidation effluent mixtures which result from olefin epoxidations using a metal catalyst and an organic hydroperoxide reactant are strongly acidic in nature. As a result of this strongly acidic nature, during subsequent distillations dehydration of by-product alcohol occurs at the distillation temperatures. Now, in accordance with the present invention, the epoxidation reaction effluent is treated prior to the distillation in order to reduce the acid characteristics thereof.

In one embodiment, there is incorporated with the reaction mixture a basic material such as sodium hydroxide in an amount sufficient to reduce the acidic characteristics of the effluent to the point where little or no alcohol dehydration takes place during subsequent distillation.

In another embodiment of the invention, the epoxidation effluent is treated with a chemical reducing agent whereby a similar effective reduction in acidity is achieved.

In still another embodiment, the effluent is subjected to hydrogenation using hydrogen and an appropriate catalyst to achieve the same acidity reduction.

Through practice of the present invention, the epoxidation effluent mixture can conveniently be treated as by distillation for the separation and recovery of various constituents without encountering the disadvantages of alcohol dehydration, the formation of high-boiling residues, and the loss of valuable products in the effluent.

The epoxidations are carried out in accordance with various techniques which are the subject of earlier patent applications. Olefins which are epoxidized to the corresponding oxirane compounds include substituted and unsubstituted aliphatic and alicyclic olefins which may be hydrocarbon, esters, alcohols, ketones, ethers, or the like. Preferred compounds are those having from about 2 to 30 carbon atoms, and preferably at least three carbon atoms. Illustrative olefins are ethylene, propylene, normal butylene, isobutylene, the pentenes, the methyl pentenes, the normal hexenes, the octenes, the dodecenes, cyclohexene, methyl cyclohexene, butadiene, styrene, methyl styrene, vinyl toluene, vinylcyclohexene, the phenyl cyclohexenes, and the like. Olefins having halogen, oxygen, sulfur and the like containing substituents can be used. Such substituted olefins are illustrated by allyl alcohol, methallyl alcohol, cyclohexanol, diallyl ether, methyl methacrylate, methyl oleate, methyl vinyl ketone, allyl chloride, and the like. In general, all olefinic materials epoxidized by methods previously employed can be epoxidized in accordance with this process including olefinically unsaturated polymers.

The lower olefins having about three or four carbon atoms in an aliphatic chain are especially advantageously epoxidized by this process.

The hydroperoxides which are employed in the invention are those having the formula ROOH wherein R is a substituted or unsubstituted alkyl, cyclaolkyl or aralkyl radical having about 3 to 20 carbon atoms. R may be a heterocyclic or like radical.

Illustrative and preferred hydroperoxides are cumene hydroperoxide, ethylbenzene hydroperoxide, tertiary butyl hydroperoxide, cyclohexanone peroxide, tetralin hydroperoxide, methyl ethyl ketone peroxide, methylcyclohexane hydroperoxide, and the like. The aralkyl hydroperoxides are especially useful.

The epoxidation catalyst includes compounds of the following: Ti, V, Cr, Se, Zr, Nb, Mo, Te, Ta, W, Re, U. These may be characterized as forming peracids or as hydroxylation catalysts. By far, the preferred catalysts are compounds of V, W, Mo, Ti, Ta, Nb, Re, and Se.

The amount of metal in solution used as catalyst in the epoxidation process can be varied widely, although as a rule it is desirable to use at least 0.00001 mols and preferably 0.002 to 0.03 mols per mol of hydroperoxide present. Amounts greater than about 0.1 mols seem to give no advantage over smaller amounts, although amounts up to 1 mol or more per mol of hydroperoxide can be employed. The catalysts remain dissolved in the reaction mixture throughout the process and can be reused in the reaction after removal of the reaction products therefrom. The molybdenum compounds include the molybdenum organic salts, the oxides such as $Mo_2O_3$, $MoO_2$, $MoO_3$, molybdic acid, the molybdenum chlorides and oxychlorides, molybdenum fluoride, phosphate, sulfide, and the like. Hetero-polyacids containing molybdenum can be used as can salts thereof; examples include phosphomolybdic acid and the sodium and potassium salts thereof. Similar or analogous compounds of the other metals mentioned may be used, as may mixtures thereof.

The catalytic components may be employed in the epoxidation reaction in the form of a compound or mixture which is initially soluble in the reaction medium. While solubility will, to some extend depend on the particular reaction medium employed, a suitably soluble substance comtemplated by the invention would include hydrocatbon soluble, organo-metallic compounds having a solubility in methanol at room temperature of at least 0.1 gram per liter. Illustrative soluble forms of the catalytic materials are the naphthenates, stearates, octoates, carbonyls and the like. Various chelates, association compounds and enol salts, such, for examples, as aceto-acetonates may also be used. Specific and preferred catalytic compounds of this type for use in the invention are the napthenates and carbonyls of molybdenum, vanadium and tungsten.

In the oxidation of the substrate, the ratio of substrate to organic peroxy compounds can vary over a wide range. Generally, mol ratios of olefinic groups in the substrates to hydroperoxide broadly in the range of 0.5:1 to 100:1, desirably 1:1 to 20:1 and preferably 2:1 to 10:1 are employed.

The concentration of hydroperoxides in the substrate oxidation reaction mixture at the beginning of the reaction will normally be one percent or more although lesser concentrations will be effective and can be used.

The substrate oxidation reaction can be carried out in the presence of a solvent, and in fact, it is generally desirable that one be used. In general, aqueous solvents are not comtemplated. Among the suitable substances are hydrocarbons, which may be aliphatic, naphthenic or aromatic, and the oxygenated derivatives of these hydrocarbons. Preferably, the solvent has the same carbon skeleton as the hydroperoxide used, so as to minimize or avoid solvent separation problems.

Temperatures which can be employed in the epoxidation can vary quite widely depending upon the reactivity and other characteristics of the particular system. Temperatures broadly in the range of about −20° to 200°C., desirably 0° to 150°C., and preferably 50° to 120°C. can be employed. The reaction is carried out at pressure conditions sufficient to maintian a liquid phase. Although sub-atmospheric pressures can be employed, pressures usually in the range of about atmospheric to about 1000 p.s.i.g. are most desirable.

In accordance with the present invention, the epoxidation effluent, which is of a catalytically acid nature insofar as alcohol dehydration is concerned, is subjected to treatment in order to reduce the acidity to the extent that alcohol dehydration is avoided during subsequent work-up.

In one, especially preferred embodiment, a basic material is incorporated with the effluent in an amount sufficient to overcome the catalytic nature of said effluent. In this embodiment of the invention, the basic material can either be added before the actual epoxidation reaction or alternatively the basic material can be added after completion of the reaction. Additionally, part can be added prior and part subsequent to the epoxidation, Insofar as this embodiment of the invention is concerned, reference is made to applicant's copending application Ser. No. 375,313, filed June 15, 1964 of which this is a continuation-in-part.

The basic substances which are employed in the present invention are alkali metal compounds or alkaline earth metal compounds. Particularly preferred are the compounds of sodium, potassium, lithium, calcium, magnesium, rubidium, cesium, strontium and barium. Compounds which are employed are those which most preferably are soluble in the reaction medium. However, insoluble forms can be employed and are effective when dispersed in the reaction medium. Organic acid compounds such as a metal acetate, naphthenate, stearate, octoate, butyrate, and the like can be employed. Additionally, inorganic salts such as Na carbonate, Mg carbonate, trisodium phosphate, and the like can also be employed. Particularly preferred species of metal salts include sodium naphthenate, potassium stearate, magnesium carbonate, and the like. Hydroxides and oxides of alkali and alkali earth metal compounds can be used. Examples are NaOH, MgO, CaO, Ca(OH)$_2$, KO and the like. Alkoxides, e.g. Na ethylate, K cumylate, Na phenate, etc. can be used. Amides such as NaNH$_2$ can be used as can quaternary ammonium salts. In general, any compound giving a basic reaction in water can be used.

The compound is employed in amounts of 0.05 to 10 mols/mol of epoxidation catalyst, desirably 0.25 to 3.0 and preferably 0.50 to 1.50.

In an alternative embodiment of the invention, the epoxidation effluent is hydrogenated in order to reduce the acid catalyst characteristics. Most preferably, the product oxirane compound is first separated as by distillation or extraction before this hydrogenation. However, it is quite possible to carry out the hydrogenation in the presence of the oxirane product.

Temperatures in the range 0° to 150°C., preferably 20° to 100°C. are employed. In this hydrogenation a suitable catalyst is employed: illustrative catalysts are platinum, copper, nickel, zinc and the like known hydrogenation catalysts. Pressures of 14.7 to 100 p.s.i.a. are preferred. Hydrogenation times of the order of 2 minutes to 1 hour are preferable.

In still another embodiment of the invention, the epoxidation effluent is reacted with a chemical reducing agent under conditions effective to reduce the acid catalyst characteristics thereof. Some typical reducing agents include sodium bisulfite, ferrous salts, compoinds containing iodide ion, ascorbic acid and other reducing agents known to the art including hydroquinone.

Appropriate temperatures are 0° to 150°C., preferably 30° to 120°C. Although it is desirable to remove the product oxirane compound prior to the chemical reduction, this is not necessary for successful practice of the invention.

The following examples illustrate the invention:

EXAMPLE I

To a pressure reaction is charged 20 grams of a 34.6 wt. % solution of alpha phenyl ethyl hydroperoxide in ethyl benzene, 20 grams of propylene and 0.2 grams of molybdenum naphthenate solution (5 wt. % Mo). The mixture is reacted for 1 hour at 110°C. Hydroperoxide conversion essentially to alpha phenyl ethanol is 97.2% and selectivity to propylene oxide based on hydroperoxide is 70.8%.

The reaction mixture which is highly acidic in nature is distilled and propylene and propylene oxide separated as overhead products from a bottoms fraction.

The characteristics of the bottoms fraction are such that on being heated to 146°C., the alpha phenyl ethanol dehydrates to styrene which instantly polymerized and is lost to residue at a dehydration rate of 244% per hour.

In accordance with the invention, the bottoms fraction is treated by the addition of sodium in the form of sodium naphthenate in amount of 0.25 mols Na per mol of Mo in the fraction.

As a result of this treatment, upon distillation at 147°C. to separate ethyl benzene and alpha phenyl ehtanol, the alpha phenyl ethanol dehydration rate is only 3.2% per hour.

EXAMPLE II

Example I is repeated except that 0.5 mols Na as sodium naphthenate is added per mol Mo. The alpha phenyl ethanol dehydration rate at 147°C. is reduced to 1.2% per hour.

EXAMPLE III

Example I is repeated through separation of propylene and propylene oxide from the bottoms fraction.

The bottoms fraction is hydrogenated at 60°C. and 100 p.s.i.g. with hydrogen over a nickel catalyst for 30 minutes. The rate of dehydration of alpha phenyl ethanol at 150°C. of the treated fraction is 0.38% per hour.

EXAMPLE IV

Example I is repeated through the separation of propylene and propylene oxide from the bottoms fraction. To the bottoms is added 0.1 mol sodium bisulfite per mol Mo. The rate of dehydration at 146°C. of alpha phenyl ethanol in the treated fraction is 9.5% per hour.

EXAMPLE V

Example I is repeated using cumene hydroperoxide in place of ethyl benzene hydroperoxide. The dehydration rate of the cumyl alcohol (dimethyl phenyl carbinol) in the epoxidation effluent after propylene and propylene oxide separation is 600% per hour at 130°C.

Sodium naphthenate is added in amount of 0.75 mols Na per mol Mo. The dehydration rate of the cumyl alcohol in the resulting mixture is reduced to 4% per hour at 130°C., 15% per hour at 150°C. and 70% per hour at 170°C.

EXAMPLE VI

Example 5 is repeated except that the mixture is hydrogenated at 60°C. and 100 p.s.i.g. with $H_2$ over a nickel catalyst after the sodium naphthenate addition. Cumyl alcohol dehydration rate in the resulting mixture is 0 at 150°C. and at 170°C.

EXAMPLE VII

Example I is repeated using vanadium naphthenate in equivalent molar amount as epoxidation catalyst. Similar results are achieved.

EXAMPLE VIII

Example I is repeated using tetrabutyl titanate in equivalent molar amount as epoxidation catalyst. Similar results are achieved.

EXAMPLE IX

Example I is repeated using tungsten carbonyl in equivalent molar amount as epoxidation catalyst. Similar results are achieved.

EXAMPLE X

Example I is repeated using tantalum naphthenate in equivalent molar amount as epoxidation catalyst. Similar results are achieved.

EXAMPLE XI

Example I is repeated using niobium naphthenate in equivalent molar amount as epoxidation catalyst. Similar results are achieved.

EXAMPLE XII

Example I is repeated using rhenium heptoxide in equivalent molar amount as epoxidation catalyst. Similar results are achieved.

EXAMPLE XIII

Example I is repeated using selenium dioxide in equivalent molar amounts as epoxidation catalyst. Similar results are achieved.

In accordance with the invention, the epoxidation effluent is treated until the acidic characteristics have been reduced to the extent that the dehydration rate of the alcohol formed by reduction of the hydroperoxide during the epoxidation is less than about 50% at 140°C., preferably less than 10% at 140°C. and desirably 0 to 5% at 140°C.

The extent of a particular treatment is conveniently determined as by periodic sampling and testing to determine the dehydration rate of the alcohol contained in the effluent.

I claim:

1. The process for treating the product mixture containing an alcohol from the epoxidation of an olefinic hydrocarbon having 2 to 30 carbon atoms with an organic hydroperoxide having the formula ROOH where R is an alkyl, cycloalkyl or carbocyclic aralkyl having 3 to 20 carbon atoms at a temperature of −20° to 200°C in the presence of a titanium, vanadium, chromium, selenium, zirconium, columbium, molybdenum, tellurium, tungsten, rhenium, or uranium catalyst, in order to reduce the acidic catalyst characteristics of said product mixture at least to the extent that the rate of dehydration of said alcohol contained therein is less than 50% per hour at 140°C which comprises the step of hydrogenating said product mixture in the presence of a hydrogenation catalyst at a temperature in the range of 0° to 150°C and at a pressure of 14.7 to 100 psia.

2. The process of claim 1, wherein the olefinic hydrocarbon is propylene and the organic hydroperoxide is ethylbenzene hydroperoxide.

3. The process of claim 1, wherein the olefinic hydrocarbon is propylene and the organic hydroperoxide is cumene hydroperoxide.

4. The process of claim 1, wherein the epoxidation catalyst is molybdenum.

5. The process for treating the product mixture containing an alcohol from the epoxidation of an olefinic hydrocarbon having 2 to 30 carbon atoms with an organic hydroperoxide having the formula ROOH where R is an alkyl, cycloalkyl or carbocyclic aralkyl having 3 to 20 carbon atoms at a temperature of −20° to 200°C in the presence of a titanium, vanadium, chromium, selenium, zirconium, columbium, molybdenum, tellurium, tantalum, tungsten, rhenium, or uranium catalyst, in order to reduce the acidic catalyst characteristics of said product mixture at least to the extent that the rate of dehydration of said alcohol contained therein is less than 50% per hour at 140°C which comprises the step of hydrogenating said product mixture at a temperature in the range of 0° to 150°C in the presence of a hydrogenation catalyst selected from the group consisting of platinum, copper, nickel and zinc.

* * * * *